US011401326B2

(12) United States Patent
Descamps et al.

(10) Patent No.: US 11,401,326 B2
(45) Date of Patent: Aug. 2, 2022

(54) METHOD OF TREATMENT OF HUMAN PAPILLOMAVIRUSES RELATED CHRONIC INFECTIONS

(71) Applicants: ASSISTANCE PUBLIQUE—HOPITAUX DE PARIS, Paris (FR); UNIVERSITE PARIS DIDEROT—PARIS 7, Paris (FR)

(72) Inventors: Vincent Descamps, Mareil-Marly (FR); Florence Brunet-Possenti, Paris (FR)

(73) Assignees: Assistance Publique—Hopitaus De Paris, Paris (FR); Universite Paris Diderot—Paris 7, Paris (FR)

( * ) Notice: Subject to any disclaimer, the term of this patent is extended or adjusted under 35 U.S.C. 154(b) by 264 days.

(21) Appl. No.: 16/303,824

(22) PCT Filed: May 24, 2017

(86) PCT No.: PCT/EP2017/062651
§ 371 (c)(1),
(2) Date: Nov. 21, 2018

(87) PCT Pub. No.: WO2017/202978
PCT Pub. Date: Nov. 30, 2017

(65) Prior Publication Data
US 2020/0308269 A1    Oct. 1, 2020

(30) Foreign Application Priority Data

May 24, 2016  (FR) ...................................... 1654637

(51) Int. Cl.
*C07K 16/24* (2006.01)
*A61P 31/20* (2006.01)

(52) U.S. Cl.
CPC ............ *C07K 16/244* (2013.01); *A61P 31/20* (2018.01)

(58) Field of Classification Search
None
See application file for complete search history.

(56) References Cited

U.S. PATENT DOCUMENTS

2012/0115821 A1*  5/2012  Jackson ............... A61P 15/00
                                                    514/159

FOREIGN PATENT DOCUMENTS

WO    WO-2006013107 A1 *  2/2006  ............. A61P 19/00

OTHER PUBLICATIONS

Partlova, Simona, et al., "Distinct patterns of intratumoral immune cell infiltrates in patients with HPV-associated compared to non-virally induced head and neck squamous cell carcinoma," Oncoimmunology 4:1, e965570, Jan. 2015 (Year: 2015).*
Wei, Lin-Huang, et al. "Interleukin-6 promotes cervical tumor growth by VEGF-dependent angiogenesis via a STAT3 pathway," Oncogene 22, 1517-1527, 2003 (Year: 2003).*
Gosmann, Christina, et al., "IL-17 suppresses immune effector functions in HPV-associated epithelial hyperplasia," Journal of Immunology, 193(5), 2248-2257, Sep. 1, 2014 (Year: 2014).*
Highlights of prescribing information for Cosentyx, Revised Jan. 2015, https://www.accessdata.fda.gov/drugsatfda_docs/label/2015/125504s000lbl.pdf (Year: 2015).*
Garde Damian, Fierce Biotech report: Novartis AIN457 (secukinumab) is the first ever IL-17A inhibitor to meet primary endpoint in two Phase III studies in psoriatic arthritis. Sep. 25, 2014. (Year: 2014).*
Chiu H-Y and Tsai T-F. The impact of secukinumab treatment on the prevalence of human papillomavirus in patients with psoriasis: A pilot study. J. Amer. Acad. Dermatol., 75, 224-226, 2016. (Year: 2016).*
International Search Report dated Jul. 28, 2017, issued in corresponding International Application No. PCT/EP201 7/062651, filed May 24, 2017, 2 pages.
Written Opinion of the International Searching Authority dated Jul. 28, 2017, issued in corresponding International Application No. PCT/EP2017/062651, filed May 24, 2017, 5 pages.
Kwok, C.S., et al., "Efficacy of topical treatments for cutaneous warts: a meta-analysis and pooled analysis of randomized controlled trials," British Journal of Dermatology 165(2):233-246, Aug. 2011.
Lipke, M.M., "An Armamentarium of Wart Treatments," Clinical Medicine & Research 4(4):273-293, Dec. 2006.
Thappa, D.M., et al., "Evolving role of immunotherapy in the treatment of refractory warts," Indian Dermatology Online Journal 7(5):364-370, Sep. 2016.
Krueger, J.G., "IL-17A is essential for cell activation and inflammatory gene circuits in subjects with psoriasis," Journal of Allergy and Clinical Immunology 130(1):145-154, Apr. 2012.
Gooderham, M., et al., "Interleukin-17 (IL-17) inhibitors in the treatment of plaque psoriasis: a review," Skin Therapy Letter 20(1):1-5, Jan. 2015.
Written Opinion of the International Searching Authority dated Jul. 28, 2017, issued in corresponding International Application No. PCT/EP2017/062651, filed May 24, 2017, 4 pages.
International Preliminary Report on Patentability dated Nov. 27, 2018, issued in corresponding International Application No. PCT/EP2017/062651, filed May 24, 2017, 1 page.

* cited by examiner

*Primary Examiner* — Elly-Gerald Stoica
(74) *Attorney, Agent, or Firm* — Christensen O'Connor Johnson Kindness PLLC

(57) ABSTRACT

Embodiments of the disclosure relate to the use of an IL-17 pathway inhibitor for treating chronic infections caused by one or more HPVs.

3 Claims, 2 Drawing Sheets

METHOD OF TREATMENT OF HUMAN PAPILLOMAVIRUSES RELATED CHRONIC INFECTIONS

The present invention relates to the treatment of chronic infections caused by human papillomaviruses. It concerns more particularly the use of an interleukin-17 pathway inhibitor to treat HPV infections.

BACKGROUND

Human Papillomavirus

Human Papillomavirus (HPV) is the most common sexually-transmitted virus. It can be transmitted by simple cutaneous or mucosal contact, which limits prevention means. Throughout the world, the number of people infected by HPV is approximately 660 million. To date, there is no effective therapy making it possible to control chronic HPV infections.

There are around 200 papillomavirus subtypes (Bernard et al., 2010), which can be divided into three large groups: (i) mucosal types with increased carcinogenic potential (HR HPV), especially HPV-16, 18, 31, 33, 45, 35, 39, 51, 52, 56, 58, 59, 68, 73, 82, 26, 53, 66; (ii) mucosal types with low carcinogenic potential (LR HPV) like HPV-6, 11, 40, 42, 43, 44, 54, 61, 70, 72, 81; (iii) cutaneous types like HPV-1, 2, 3, 4 and 5. Different HPV subtypes can be involved in the occurrence of benign lesions (warts, condylomata . . . ) but also pre-neoplastic lesions and invasive cancers.

Warts and condylomata are a clinical translation of chronic cutaneous non-oncogenic HPV infections.

Pre-neoplastic lesions, as well as invasive cancers linked to HPV, are induced by high oncogenic risk HPVs (HR HPV). Given the very high frequency of infection by HR HPVs, it is estimated that mucosal cancers induced by HPV, all sites combined (gynaecological, anal, ENT and external male genital organs) represent 5 to 10% of all the cancers diagnosed in the world. Among these cancers, the gynaecological sites are the most frequent and the pathogenic role of HR HPVs is now well known: 99.9% of squamous cancers of the cervical canal are induced by chronic HR HPV infection. The gynaecological monitoring of women forms part of the priorities of preventative medicine and the encouragement of having regular smear tests, as well as the development of HPV tests bear witness to the high involvement of public health authorities in the screening and prevention of cervical cancers. Moreover, HR HPV viruses are also responsible for other mucosal cancers. This is the case of anal cancers, which are almost systematically associated with the presence of HR HPV, and of which the prevalence does not stop increasing (Nelson et al., 2013). ENT cancers are also closely linked to infections by HR HPV (Mehanna et al., 2013), in particular, oropharyngeal sites for which the infection by these viruses represents the only etiopathogenic factor in 70% of cases (Chaturvedi et al., 2011). Finally, the lesions induced by HR HPVs at the level of the external male genital organs (Stratton and Culkin, 2016), although not very frequent, can also evolve towards a cancer and this, especially because they are widely under-diagnosed.

HPV Cutaneous Infection

HPVs with cutaneous tropism are mainly responsible for benign tumour lesions: common warts (in particular on fingers), flat warts, mosaic warts, myrmecia warts (deep wart), or papillomas and condylomata. Although these lesions are considered as benign, they constitute a very frequent basis for consultation, because of their painful character and because of the social discomfort they frequently cause. The most frequently proposed therapies are topical (salicylate Vaseline, Imiquimod, cryotherapy with liquid nitrogen). These treatments are often unsatisfactory as they have no effect on the viral replication, which explains the chronicity and the frequent recurrences of these lesions (Kwok et al., 2011).

In immunodepressed patients, in particular transplant patients or patients who are HIV seropositive, abundant forms of warts and/or condylomata are frequent and particularly debilitating (Sterling et al., 2001).

A particular group of cutaneous HPVs (HPV 5 and 8 mainly) is associated with a rare genodermatosis, epidermodysplasia verruciformis (EV). This disease is responsible for a particular vulnerability to infection by these HPVs starting with multiple flat warts which appear early in life and can evolve towards pre-carcinomatous lesions (Bowen's disease) and then towards invasive squamous carcinoma. These lesions appear preferably in a photo-exposed zone witnessing of the interaction of several factors: HPV, exposure to ultraviolet radiations, genetic predisposition. It is useful to note that EV tables can be observed in case of immunodepression (infection by HIV, transplants). This immunodepression thus exposes, like the genetic predisposition to EV, a vulnerability to infection from these HPVs associated with the EV and to the risk of developing cutaneous squamous carcinoma. This is particularly illustrated in case of congenital HIV infection with EV tables in young children infected by HIV (Lowe et al., 2012).

Independently of the role of HPVs in the EV or in the carcinomas of immunodepressed patients, the participation of these viruses has been discussed in the physiopathology of psoriasis. Indeed, the prevalence of the infection by these HPVs associated with the EV is more important in the skin of patients suffering from psoriasis, which makes the role of these viruses plausible as an alloantigen inducing or sustaining psoriasis lesions (Mahé et al., 2003).

Mucosal Infections by HPV with Low Oncogenic Risk (LR HPV)

These infections translated clinically into the appearance of papillomatous lesions localised in the genital and anal area. A frequent ENT manifestation of this type of infection is laryngeal papillomatosis (Li et al., 2015a), which more particularly affects children and which can, in certain cases, lead to a blocking of the airways. The treatment of anogenital lesions is based on the destruction by liquid nitrogen or laser vaporisation. For ENT sites, surgical removal can also be proposed. All these treatments have a limited effectiveness as HPV infection remains latent and relapses are therefore frequent.

Gynaecological HR HPV Infections

HPV infection is an important source of gynaecological pathologies, cervical cancer being the second most frequent cancer among women on a global scale (Source: WHO). Currently in France, there are 3000 new cases per year and 1000 annual deaths relating to this cancer (Source: National Cancer Institute).

Non-oncogenic HPV infections are distinguished from oncogenic HPV infections, called high risk (HR). Among the most commonly found non-oncogenic HPVs are HPVs 6 and 11 originating from condylomata, which could be located on the vulva, the vagina or the cervix. The two main HR HPVs involved in 70% of pre-cancerous and cancerous lesions of the cervix (Lowy and Schiller, 2012), but also of the vagina and of the vulva, are HPVs 16 and 18.

The cervical HPV infection is developed in the first years of sexual activity and concerns the vast majority of women:

it is the most frequent sexually transmitted infection. Most infected women spontaneously get rid of the HPV in 6 to 24 months, the prevalence of the infection clearly decreasing after 30 years. However, for a minority of women, the infection can persist, leading in certain cases, to the appearance of pre-cancerous cervical lesions: CINs (cervical intraepithelial neoplasia) (Schiffman et al., 2007). There again, most of these lesions will spontaneously regress with the elimination of the virus, but some will persist for several years, then evolve to increasingly severe stages (CIN1 to CIN3) leading to invasive cancer (most often, the squamous type) 10 to 15 years after the appearance of the first CINs. The development is systematically as follows: type 1 endocervical neoplasia (CIN1), then CIN2 and finally CIN3 (Baseman and Koutsky, 2005). It must be noted, that the natural history of HR HPV infections of other mucosal sites is similar to that described for the cervix, with a continuity between pre-cancerous lesions and invasive cancer and regression of lesions in case of spontaneous elimination of HPVs (Nobbenhuis et al., 2001).

In France, the algorithm for managing pre-neoplastic cervical lesions is based on the level of severity. Low-level lesions (CIN1) have a low potential for developing towards an invasive cancer, it is therefore recommended not to treat and to carry out a close monitoring. For high-level lesions (CIN2 and 3), the transformation risk is more important, the current therapeutic attitude of gynaecologists consists of a treatment by cryotherapy or laser vaporisation of the cervix for CIN2s and cervical conisation for CIN3s, less frequently for CIN2s. Managing CINs remains the subject of debate because of the possible regression thereof in case of spontaneous viral clearance, but as a precaution, clinicians opt most often for a systemic treatment. These treatments can lead to complications, in particular with cervical conisation, of the cervical stenosis type and can increase the risk of premature birth (Sozen et al., 2014). Moreover, these procedures do not guarantee there being no recurrence (in 5 to 10% of cases) because of the limited character of these treatments, which relate to the destruction of atypical cells, but which have no effect on the surrounding mucosa that remains infected by HPV.

Pre-cancerous and cancerous vulvovaginal lesions are rarer but are also linked to 70% of cases with the HPV infection.

ENT Infections by HR HPV

Although squamous carcinomas of the upper aerodigestive tract are most often associated with alcohol and tobacco intoxication, in certain sites, in particular oropharyngeal sites, oncogenic subtypes of the HPV virus (mainly HPV16 and HPV18) are frequently the only identified environmental factors. The prevalence of HR HPV infections in ENT tumours varies, according to the geographic origin of the patient and the anatomic localisation, with a greater frequency of these infections at the level of the oropharynx (tonsils and base of the tongue). In tonsil cancers, the presence of an HR HPV is detected in 50 to 70% of cases (Ang et al., 2010; D'Souza et al., 2007; Kreimer et al., 2005; Mork et al., 2001; Syrjänen, 2010).

These figures are in accordance with the results of several large international studies confirming the presence of this virus in at least 30% of tonsil cancers. Thus, one of these studies based on 5046 cases of ENT tumours (Kreimer et al., 2005), all sites combined, relates to a prevalence of HR HPV infection of 25.9%, with a preferential site at the level of the oropharynx: 35.6% versus 23.5% for the oral cavity and 24% for the larynx.

Anal Infections by HR HPV

Anal cancer is rare and currently represents less than 5% of colorectal cancers, but its incidence is growing. It occurs most often after the age of 60 and concerns more frequently women. Just like for cervical cancers, the main etiological factor is chronic HR HPV infection, present in 95% of cases of pre-cancerous lesions (Anal Intraepithelial Neoplasia or AIN) which, in the absence of treatment (laser vaporisation, Imiquimod, surgical removal, etc.) can evolve towards an invasive cancer (Weis, 2013). The prevalence of AINs among the general population is currently not well known, because of the absence of screening. The male homosexual population is particularly at risk of developing AINs.

Urological Infections Linked to HR HPV

Squamous carcinomas of external male genital organs, and more particularly of the glans, are not very frequent but are associated in 75% of cases to an HR HPV infection, and have a natural history, similar to that described for the cervix, with the development of penile intraepithelial neoplasia (PIN) towards an invasive carcinoma. Moreover, the coronal sulcus constitutes a "reservoir" for HPV viruses, as evidenced by the lowest prevalence of viral porting in circumcised men compared with non-circumcised men. This reservoir can constitute a self-inoculating source of HPVs towards other mucosal sites, and possibly contributes to the chronicity of HPV infections in sexual partners (Martin-Ezquerra et al., 2012).

Mucosal Infections by HR HPV in Immunodepressed Patients

Regardless of the nature of the immunodepression (HIV, immunosuppressive treatments, etc.), the prevalence of pre-neoplastic mucosal lesions and therefore of invasive cancers is broadly greater than that of the general population, for all sites combined, both anogenital and ENT sites (Katz et al., 2014; Mazanowska et al., 2013; Sunesen et al., 2010).

Among HIV-infected patients, the prevalence of the HR HPV infection in anogenital sites is particularly high (60% in women and more than 90% in homosexual men). HPV infections are often multiple, associating several oncogenic viral genotypes and the persistence of the infection is more frequent, which encourages the occurrence of pre-cancerous and cancerous lesions. Thus, cervical lesions in seropositive women are very frequent, which justifies an annual screening of cervical cancer among this population. Likewise, the risk of invasive squamous anal cancer is very clearly increased in the HIV+ male homosexual population. It is therefore recommended to propose a regular screening with an anoscopy, in particular among men who have multiple partners. The increase of the impact of lesions induced by HR HPVs is proportional to the duration of the infection by HIV: in patients who have been infected for more than 15 years, the incidence is 12 times greater than that observed in patients who have been infected for less than five years, which is the reflection of the natural history of HPVs, but also of the low impact of antiretroviral drugs on chronic HPV infections (Piketty et al., 2013).

Vaccination Against HPVs

Two vaccines are currently available on the market: one directed against HPVs 16 and 18 (commercialised under the name of Cervarix) and the other against HPVs 16, 18, 6 and 11 (commercialised under the name of Gardasil). In France, this vaccination is recommended since 2008, only for girls aged from 11 to 14. Although this vaccine is paid for by Social Security, the immunisation coverage remains less than 25%.

The anti-HPV vaccination is a key element in the fight against cervical cancer, but because of its recent implementation, the low immunisation coverage and the natural history of HPV infections, its impact on the occurrence of lesions caused by HPVs will not be felt for another decade. Moreover, these vaccines only protect against a few HPV genotypes. Current recommendations are therefore to continue cervical cancer screening among women who have been vaccinated.

IL-17 Pathway Inhibitors

Interleukine-17 (IL-17) is a pro-inflammatory cytokine produced by type 17 T-helper cells (Th 17). Six isoforms have been identified (IL-17A to IL-17F), as well as five ubiquitous expression receptors (IL-17RA to IL-17RE) (Gaffen, 2009).

The activation of the IL-17 pathway during the connection between IL-17 and its receptor leads to the expression of pro-inflammatory genes, like for example those coding for chemokines responsible for the induction of immune cells (neutrophils, lymphocytes, etc.). Within this family, IL-17A plays a prominent role, because of its powerful pro-inflammatory effects, and because of this, it is the best described currently (Beringer et al., 2016). Biologically, IL-17A is presented as a homodimer (A/A) or a heterodimer (A/F) associated with IL-17F.

This family of interleukins is involved in a large number of inflammatory pathologies, such as psoriasis, rheumatoid arthritis, and inflammatory intestinal diseases.

Secukinumab (developed by Novartis) is an IgG1 type monoclonal antibody that selectively binds to IL-17A. This molecule has been developed following the highlighting of increased concentrations of IL-17 in psoriatic lesions, as well as in the serum of patients suffering from psoriasis; this bears witness to the role of IL-17 in deregulating the skin's immune system, a key phenomenon of the physiopathology of psoriasis. The neutralisation of IL-17A is a new therapeutic approach for psoriasis making it possible to obtain very promising clinical results with an excellent tolerance profile (Langley et al., 2014). Several therapeutic approaches aiming at using an IL-17 pathway inhibitor to treat psoriasis have therefore been developed; some of these are still undergoing clinical trials, while others have obtained a marketing authorisation.

IL-17 is also involved in defending against certain fungal microbial and bacterial agents (Bär et al., 2014), as well as in the carcinogenesis of certain tumours (Wang et al., 2009).

Several in vitro studies have examined the link between IL-17 and HPV infection with high oncogenic risk (HR HPV), highlighting the increased rates of IL-17 in cancer tissues linked to HPV (Chang et al., 2010; Li et al., 2015). These results argue in favour of a pro-carcinogenic effect of IL-17 via the induction of an inflammatory microenvironment. Moreover, an immunosuppressive action of this interleukin has also been demonstrated on the epithelial hyperplasia tissue induced by the HR HPV infection (Gosmann et al., 2014).

However, no clinical or biological data is currently available concerning the role of IL-17 in chronic non-oncogenic HPV skin infections. To date, there is also no data concerning the in vitro or in vivo effect of IL-17 pathway inhibitors on HPV infections.

In this context, the inventors propose to use an IL-17 pathway inhibitor to treat chronic HPV infections, especially non-oncogenic infections. This new therapeutic approach is based (i) on the one hand, on the abovementioned recent discoveries relating to the role of IL-17 and (ii) on the other hand, on several clinical observations relating to the effect of an anti-IL-17 on the porting of different types of mucosal HPV (LR HPV and HR HPV), as well as on benign cutaneous lesions (warts) and pre-neoplastic cervical lesions, which are clinical manifestations exclusively linked to the HPV infection.

These clinical observations show that the anti-IL-17, especially specific antibodies that bind IL-17A, have an effect both on cutaneous HPVs and on HR or LR mucosal HPVs.

Based on these results, supported especially by data from the literature concerning the involvement of IL-17 in HR HPV infections, the inventors consider that using an IL-17 pathway inhibitor constitutes a very promising therapeutic approach for HPV infections, regardless of the clinical site and the HPV types in question.

These therapeutic approaches have proved to be particularly useful concerning chronic HR HPV mucosal infections, with the purpose of decreasing the risk of HPV-induced lesions evolving towards invasive cancers, in particular cervical cancer, as well as the decrease of the recurrence risk after treatment of the lesions induced by HR HPV.

DETAILED DESCRIPTION OF THE INVENTION

The first purpose of the present invention is the use of an IL-17 pathway inhibitor to treat chronic infections caused by one or more HPVs.

Chronic HPV infections cover several diseases which differ according to the oncogenic nature, or lack thereof, of the HPVs involved, and according to their cutaneous or mucosal localisation. The term "chronic HPV infection" is used in the present invention to describe a chronic keratinocyte infection by one or more HPV subtypes.

Skin damage can result from infections by non-oncogenic HPVs, as in the case of warts and papillomas; or infections by oncogenic HPVs, as in the case of epidermodysplasia verruciformis (EVR).

Mucosal damage can also result from infections by non-oncogenic HPVs, as in the case of anogenital condylomata and laryngeal papillomatosis; or infections by oncogenic HPVs, as in the case of pre-neoplastic lesions and squamous cancers of the cervix, the ENT area, the anus and the glans.

Thus, in a preferred embodiment, the invention consists of using an IL-17 pathway inhibitor to treat a chronic infection caused by one or more HPVs selected from among warts, condylomata, laryngeal papillomatosis, epidermodysplasia verruciformis, as well as pre-neoplastic lesions and squamous cancers located on gynaecological, ENT, anal and penile sites. In a particularly preferred embodiment, the IL-17 pathway inhibitor is an IL-17A pathway inhibitor.

In a specific embodiment, the invention consists in administering an IL-17 pathway inhibitor to a patient suffering from warts, with the aim of making them disappear. The effectiveness of such a treatment is reported in the clinical case presented in the experiment section. Indeed, the administration of an anti-IL-17A antibody to patients suffering from warts having resisted conventional treatments has made it possible for a significant, even complete regression of the cutaneous lesion in three months.

In other words, this clinical result makes it possible to propose the administration of an IL-17 pathway inhibitor, in particular an IL-17A inhibitor, particularly advantageously, of a specific antibody that binds IL-17A, to treat chronic non-oncogenic HPV cutaneous and mucosal infections responsible for clinical manifestations resisting conventional treatments such as warts, condylomata and papillomas.

In another particular embodiment, the IL-17 pathway inhibitor, for example an anti-IL-17A, particularly advantageously of a specific antibody that binds IL-17A, is administered to a patient infected by one or more oncogenic HPVs and suffering from pre-neoplastic cervical lesions (CINs) in order to achieve the regression of these lesions without resorting to invasive therapeutic protocols. This approach relates to treating chronic oncogenic HPV mucosal infections to avoid the development thereof towards an invasive cancer.

In another specific embodiment, the IL-17 pathway inhibitor is administered systemically to a patient chronically infected by one or more oncogenic HPVs with presence of CIN.

In another embodiment, this inhibitor can be administered for the purpose of managing invasive cervical cancers. The aim of such a treatment is to decrease the risk of tumour recurrence by limiting the replication of persistent latent HPV after treatment of an invasive cancer. The decrease of the risk of recurrence relates both to the recurrence at the initial site and in the periphery of the lesion.

In another embodiment, the invention consists in administering an IL-17 pathway inhibitor, for example an anti-IL-17A, to an immunodepressed subject suffering from chronic mucosal infections caused by one or more HR HPVs. These subjects indeed present an increased risk of developing cancerous lesions in case of persistent HR HPV infection; the treatment proposed would therefore make it possible, by controlling the viral infection, to limit this risk. Immunodepressed patients who could benefit from such a treatment are, in particular, subjects infected by HIV and transplant subjects.

In another embodiment, the invention consists in administering an IL-17 pathway inhibitor to a subject suffering from EV. An IL-17 pathway inhibitor should make it possible to control the HPV infection associated with the EV and to prevent the development of benign and malign cutaneous lesions associated with these viruses. The EV could constitute an almost-experimental model to judge the effectiveness of this therapeutic approach.

In the context of the invention, the treatment of the viral infection means controlling the viral replication and the regression of clinical and cellular lesions induced by chronic HPV infection.

Controlling the viral HPV infection by an IL-17 pathway inhibitor can be attributed to two modes of action:
  Immunomodulation by opposing the local immunosuppressive effect of IL-17, which favours the infection and the replication of HPV viruses. In this case, the effect of the IL-17 pathway inhibitor is to limit the viral replication, regardless of the HPV types involved and their site, by re-establishing the local immunity.
  Anti-proliferative effect by inhibiting the direct effect of IL-17 on the proliferation and differentiation of keratinocytes, as in the case of treating psoriasis. In this case, the IL-17 pathway inhibitor decreases the proliferation of infected keratinocytes, which leads to the decrease of the viral HPV load. With the vital infection being limited, the proliferation of keratinocytes will also amplify the phenomenon of viral control.

In the present invention, the term "IL-17 pathway inhibitor" is used to describe any compound or any molecule capable of inhibiting the signalling pathway of IL-17. In particular, such an inhibitor or antagonist can be an antibody or an antibody fragment directed against IL-17 or against IL-17 receptor (IL-17R), a soluble receptor of IL-17, a chemical compound or any chimeric agent. In a preferred embodiment, the IL-17 inhibitor is a specific antagonistic antibody of IL-17. This IL-17 pathway inhibitor can specifically bind to IL-17A, IL-17B, IL-17C, IL-17D, IL-17E or IL-17F, or to their respective receptors. In a preferred embodiment, such an inhibitor is a specific antibody that binds IL-17A or a specific soluble receptor of IL-17A.

Numerous IL-17 pathway inhibitors are available, among which specific anti-IL-17 antibodies; as an example of anti-IL-17 antibodies, Secukinumab (Novartis), Ixekizumab (Eli Lilly) and ANB004 (AnaptysBio Inc.) can be cited. Other antibodies targeting the receptor of IL-17 have been developed, such as Brodalumab (Amgen).

In the present invention, the term "antibody" is used to describe a monoclonal antibody or an antibody fragment, for example the fragments $F(ab')_2$, $F(ab)$ or scFv specifically binding to IL-17 or any peptide comprising a domain of the initial antibody recognising IL-17. The term "antibody" also covers variants of antibodies, well known to a person skilled in the art, such as chimeric or humanised antibodies.

In the context of the present invention, the IL-17 pathway inhibitor can be locally administered, intralesionally, or systemically.

As an example of treatment using an anti-IL-17 antibody, Secukinumab can be administered systemically, by subcutaneous injection with a 300 mg dose for five consecutive weeks, then at the rate of one injection every four weeks. This treatment regimen is that which has been applied to patients in whom the administration of an anti-IL-17A has made it possible for a significant, even complete regression of warts in three months; these cases are presented in detail in the experiment section. This same treatment regimen corresponds to that which has been followed by patients in whom the administration of an anti-IL-17A has made it possible to decrease the genital porting of both HR and LR HPV in three months; these cases are presented in detail in the experiment section.

This regimen also corresponds to that followed by a patient presenting cytological anomalies on the smear test performed during the start of treatment by anti-IL-17-A, lesions which have totally regressed after 4.5 months of treatment.

It must be noted, that the dosage and the administration method can be adapted to the type of inhibitor used and according to the lesions to be treated; a person skilled in the art, and in particular, the doctor responsible for the patient, will know how to determine the appropriate dose, as well as the periodicity of the administration.

In certain cases of localised lesions, it could be interesting to inject the anti-IL-17 locally, and not systemically, which would make it possible to decrease the dose and therefore the cost of the treatment.

In addition, it is possible to consider re-administering an anti-IL-17 in case of reappearance of cutaneous or mucosal lesions caused by HPV as these antibodies have a good tolerance profile.

The present invention is described in a specific embodiment using the following example. This has the sole aim of illustrating the invention and cannot, in any case, be considered as limiting the scope of the invention.

EXPERIMENTAL DATA

Example 1

Clinical case: Complete disappearance of a skin wart during a treatment by Secukinumab.

Figure 1:
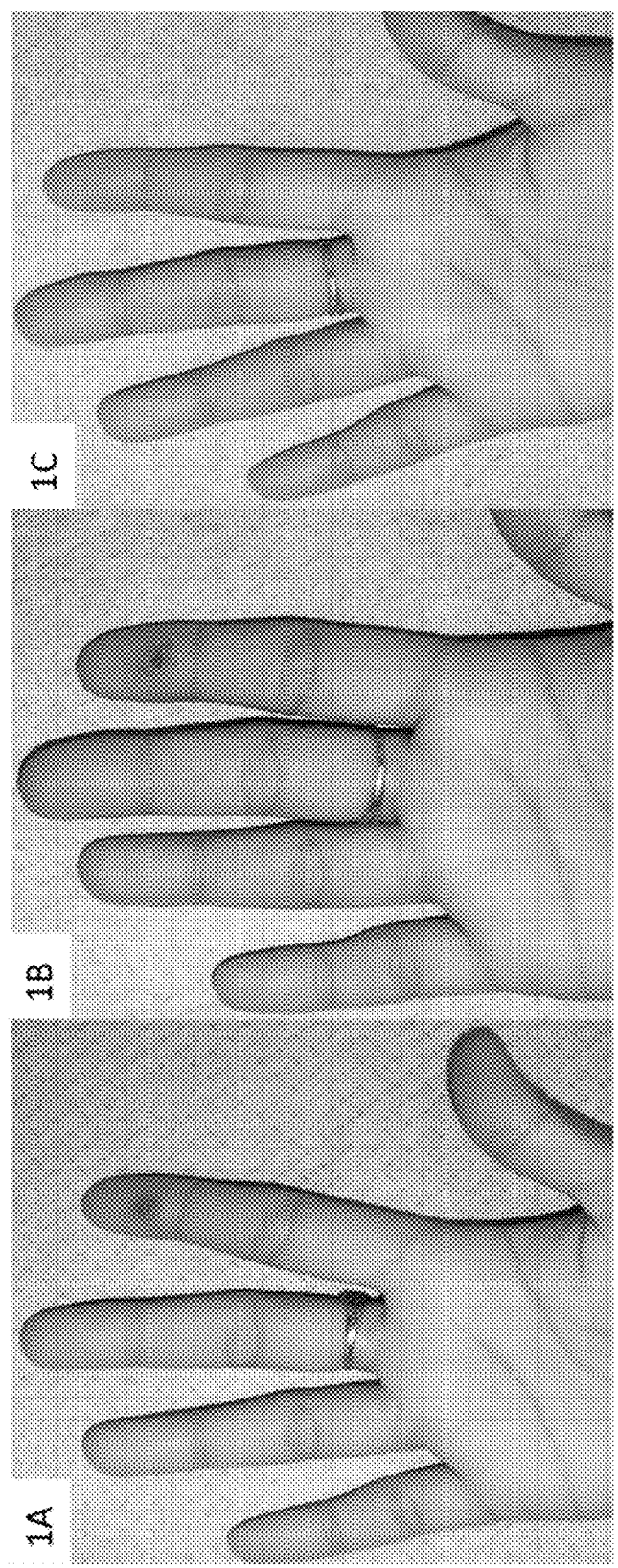
FIG. 1: Development of a wart located on the index finger of a female patient treated by Secukinumab. 1A: before treatment; 1B: after one month of treatment; 1C: after two months of treatment.

Background: The clinical observation concerns a 29-year old patient having consulted for psoriasis with a PASI index evaluated at 14.5, and who had resisted several lines of therapy, especially phototherapy and systemic treatments by Acitretin and Methotrexate. Moreover, this patient presented a wart localised on the pad of the right index finger which had been evolving for eight months, treated iteratively by cryotherapy and applications of salicylic acid, without success (FIG. 1A).

Treatment: For the purpose of managing psoriasis, a treatment by Secukinumab (anti-IL-17, developed by Novartis) was initiated according to the following regimen: weekly subcutaneous injections with a 300 mg dose for five weeks, then monthly injection.

Result: The monitoring highlighted, after one month of treatment, a clear improvement of the psoriasis, as well as a decrease of the size of the wart (FIG. 1B). Two months after the start of treatment by Secukinumab, the complete disappearance of psoriasis lesions was accompanied by the total regression of the wart (FIG. 1C), without any topical treatment having been applied on this wart. The re-evaluation after six months of treatment found no recurrence of the lesion.

Example 2

Clinical cases: Complete disappearance and significant regression of skin warts during a treatment by Secukinumab.

Background: The following clinical observations relate to three patients suffering from psoriasis and warts.

Treatment: For the purpose of managing psoriasis, a treatment by Secukinumab (anti-IL-17, developed by Novartis) was initiated according to the following regimen: weekly subcutaneous injections with a 300 mg dose for five weeks, then monthly injection.

Figure 2:
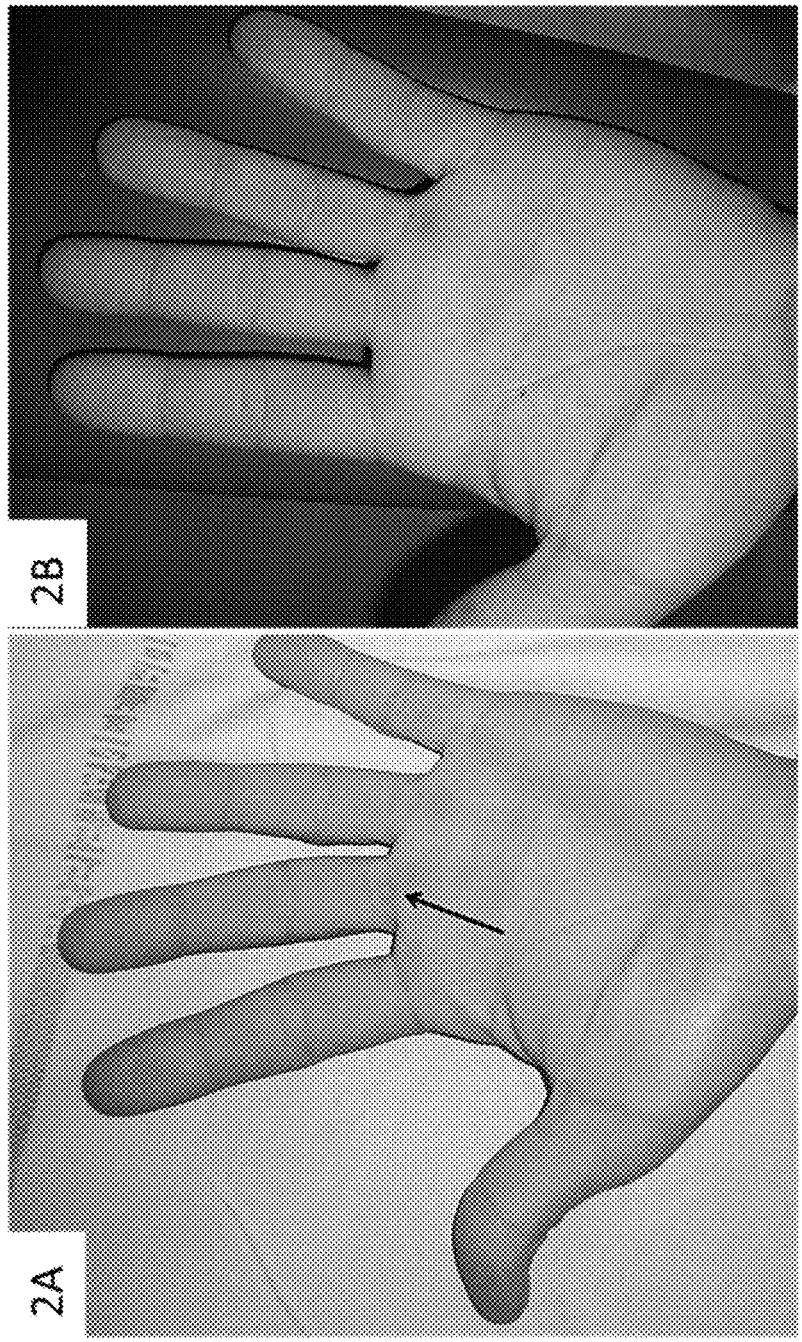
FIG. 2: Development of a finger wart located on the bottom of the middle finger of a patient treated by Secukinumab. 2A: before treatment; 2B: after three months of treatment.

Result: The monitoring highlighted, after three months of treatment, a complete regression of the warts in a patient (FIG. 2), as well as a clear decrease of the size of the wart (regression of around 50% of the surface area of the warts) in the two other patients.

Example 3

Clinical Cases: Decrease of the Number of Mucosal HPVs and Regression of Cellular Anomalies Induced by HR HPV During a Treatment by Secukinumab.

Background: The following clinical observations relate to three patients suffering from psoriasis and presenting a multiple HPV infection (HR and LR HPV), at the level of the coronal sulcus for two patients and at the vulvovaginal and cervical level for one patient. The female patient in question also presented an abnormal smear test at the start of the treatment (ASCUS smear according to the Bethesda classification), resulting from the HR HPV infection.

Treatment: For the purpose of managing the psoriasis, a treatment by Secukinumab (anti-IL-17, developed by Novartis) was initiated according to the following regimen: weekly subcutaneous injections with a 300 mg dose for five weeks, then monthly injection.

Result: The monitoring highlighted, after three months of treatment, a decrease of the number of mucosal HPV types for the three patients (see Table 1).

Concerning the female patient, the smear test at three months of treatment showed the persistence of cytological anomalies (HSIL smear according to the Bethesda classification), and then the test colposcopy after 4.5 months of treatment highlighted the complete regression of the cellular anomalies.

TABLE 1

|  | Mucosal sample before introducing Secukinumab | Mucosal sample at the third month of treatment by Secukinumab |
|---|---|---|
| Patient A Vulvovaginal site | HR HPV: 58, 68, 73 LR HPV: 40, 42, 70 | HR HPV: 58, 68 LR HPV: 42, 70 |
| Patient A cervical site | HR HPV: 58, 68 LR HPV: 40, 70 | HR HPV: 58, 68 LR HPV: 70 |
| Patient B Coronal site | HR HPV: 18, 52, 68, 73 LR HPV: 42 | HR HPV: none LR HPV: 42 |
| Patient C Coronal site | HR HPV: 35, 51, 52, 68 LR HPV: none | HR HPV: none LR HPV: none |

This data shows that after only three months of treatment, the number of HR and LR HPV types, in other words, mucosal HPV infection, had decreased in these three patients. The result observed in the female patient after 4.5 months of treatment also argues in favour of a favourable effect of the anti-IL-17A, not only on the HPV infection, but also on the pre-neoplastic lesions induced by the mucosal HR HPVs.

It has been shown that the administration of Secukinumab has an effect on cutaneous HPV infections (Chiu et al., 2016). This article highlights a decrease of the cutaneous HPVs during the treatment, with a statistical significance from the sixth month. Regarding Chiu et al., it is probable that the effect on the mucosal HPV infection observed at only three months will be confirmed and amplified by extending the treatment over time.

These results thus demonstrate the therapeutic effect of an anti-IL-17, in particular an anti-IL-17A, on both LR HPV and HR HPV infections, as well as on pre-neoplastic lesions induced by these HPVs.

BIBLIOGRAPHIC REFERENCES

Ang, K. K., Harris, J., Wheeler, R., Weber, R., Rosenthal, D. I., Nguyen-Tan, P. F., Westra, W. H., Chung, C. H., Jordan, R. C., Lu, C., et al. (2010). Human papillomavirus and survival of patients with oropharyngeal cancer. N. Engl. J. Med. 363, 24-35.

Bär, E., Whitney, P. G., Moor, K., Reis e Sousa, C., and LeibundGut-Landmann, S. (2014). IL-17 Regulates Systemic Fungal Immunity by Controlling the Functional Competence of NK Cells. Immunity 40, 117-127.

Baseman, J. G., and Koutsky, L. A. (2005). The epidemiology of human papillomavirus infections. J. Clin. Virol. Off. Publ. Pan Am. Soc. Clin. Virol. 32 *Suppl* 1, S16-24.

Beringer, A., Noack, M., and Miossec, P. (2016). IL-17 in Chronic Inflammation: From Discovery to Targeting. Trends Mol. Med. 22, 230-241.

Bernard, H.-U., Burk, R. D., Chen, Z., van Doorslaer, K., zur Hausen, H., and de Villiers, E.-M. (2010). Classification of Papillomaviruses (PVs) Based on 189 PV Types and Proposal of Taxonomic Amendments. Virology 401, 70-79.

Chang, Y.-H., Yu, C.-W., Lai, L.-C., Tsao, C.-H., Ho, K.-T., Yang, S.-C., Lee, H., Cheng, Y.-W., Wu, T.-C., and Shiau, M.-Y. (2010). Up-regulation of interleukin-17 expression by human papillomavirus type 16 E6 in nonsmall cell lung cancer. Cancer 116, 4800-4809.

Chaturvedi, A. K., Engels, E. A., Pfeiffer, R. M., Hernandez, B. Y., Xiao, W., Kim, E., Jiang, B., Goodman, M. T., Sibug-Saber, M., Cozen, W., et al. (2011). Human papillomavirus and rising oropharyngeal cancer incidence in the United States. J. Clin. Oncol. Off. J. Am. Soc. Clin. Oncol. 29, 4294-4301.

Chiu, H. S., Tasi, T. F. (2016). The impact of secukinumab treatment on the prevalence of human papillomavirus in patients with psoriasis: A pilot study. J. AM. Acad. Dermatol. 224-226. 'Souza, G., Kreimer, A. R., Viscidi, R., Pawlita, M., Fakhry, C., Koch, W. M., Westra, W. H., and Gillison, M. L. (2007). Case-control study of human papillomavirus and oropharyngeal cancer. N. Engl. J. Med. 356, 1944-1956.

Gaffen, S. L. (2009). Structure and signalling in the IL-17 receptor family. Nat. Rev. Immunol. 9, 556-567.

Gosmann, C., Mattarollo, S. R., Bridge, J. A., Frazer, I. H., and Blumenthal, A. (2014). IL-17 suppresses immune effector functions in human papillomavirus-associated epithelial hyperplasia. J. Immunol. Baltim. Md. 1950/93, 2248-2257.

Katz, J., Nadim Islam, M., Bhattacharyya, I., Sandow, P., and Moreb, J. S. (2014). Oral squamous cell carcinoma positive for p16/human papilloma virus in post allogeneic stem cell transplantation: 2 cases and review of the literature. Oral Surg. Oral Med. Oral Pathol. Oral Radiol. 118, e74-e78.

Kreimer, A. R., Clifford, G. M., Boyle, P., and Franceschi, S. (2005a). Human papillomavirus types in head and neck squamous cell carcinomas worldwide: a systematic review. Cancer Epidemiol. Biomark. Prev. Publ. Am. Assoc. Cancer Res. Cosponsored Am. Soc. Prev. Oncol. 14, 467-475.

Kreimer, A. R., Clifford, G. M., Boyle, P., and Franceschi, S. (2005b). Human papillomavirus types in head and neck squamous cell carcinomas worldwide: a systematic review. Cancer Epidemiol. Biomark. Prey. Publ. Am. Assoc. Cancer Res. Cosponsored Am. Soc. Prev. Oncol. 14, 467-475.

Kwok, C. S., Holland, R., and Gibbs, S. (2011). Efficacy of topical treatments for cutaneous warts: a meta-analysis and pooled analysis of randomized controlled trials. Br. J. Dermatol. 165, 233-246.

Li, J., Zhang, T.-Y., Tan, L.-T., Wang, S.-Y., Chen, Y.-Y., Tian, J.-Y., Da, W.-Y., He, P., and Zhao, Y.-M. (2015a). Expression of human papillomavirus and prognosis of juvenile laryngeal papilloma. Int. J. Clin. Exp. Med. 8, 15521-15527.

Li, Y. X., Zhang, L., Simayi, D., Zhang, N., Tao, L., Yang, L., Zhao, J., Chen, Y. Z., Li, F., and Zhang, W. J. (2015b). Human papillomavirus infection correlates with inflammatory Stat3 signaling activity and IL-17 level in patients with colorectal cancer. PloS One 10, e0118391.

Lowe, S. M., Katsidzira, L., Meys, R., Sterling, J. C., de Koning, M., Quint, W., Nathoo, K., Munyati, S., Ndhlovu, C. E., Salisbury, J. R., et al. (2012). Acquired epidermodysplasia verruciformis due to multiple and unusual HPV infection among vertically-infected, HIV-positive adolescents in Zimbabwe. Clin. Infect. Dis. Off. Publ. Infect. Dis. Soc. Am. 54, e119-123.

Lowy, D. R., and Schiller, J. T. (2012). Reducing HPV-associated cancer globally. Cancer Prev. Res. Phila. Pa. 5, 18-23.

Mahé, E., Bodemer, C., Descamps, V., Mahé, I., Crickx, B., De Prost, Y., and Favre, M. (2003). High frequency of detection of human papillomaviruses associated with epidermodysplasia verruciformis in children with psoriasis. Br. J. Dermatol. 149, 819-825.

Martin-Ezquerra, G., Fuste, P., Larrazabal, F., Lloveras, B., Fernandez-Casado, A., Belosillo, B., Mancebo, G., Masferrer, E., Segura, S., Carreras, R., et al. (2012). Incidence of human papillomavirus infection in male sexual partners of women diagnosed with CIN II-III. Eur. J. Dermatol. EJD 22, 200-204.

Mazanowska, N., Pietrzak, B., Kamiński, P., Ekiel, A., Martirosian, G., Jabiry-Zieniewicz, Z., and Wielgoś, M. (2013). Prevalence of cervical high-risk human papillomavirus infections in kidney graft recipients. Ann. Transplant. 18, 656-660.

Mehanna, H., Beech, T., Nicholson, T., El-Hariry, I., McConkey, C., Paleri, V., and Roberts, S. (2013). Prevalence of human papillomavirus in oropharyngeal and nonoropharyngeal head and neck cancer—systematic review and meta-analysis of trends by time and region. Head Neck 35, 747-755.

Mork, J., Lie, A. K., Glattre, E., Hallmans, G., Jellum, E., Koskela, P., Møller, B., Pukkala, E., Schiller, J. T., Youngman, L., et al. (2001). Human papillomavirus infection as a risk factor for squamous-cell carcinoma of the head and neck. N. Engl. J. Med. 344, 1125-1131.

Nelson, R. A., Levine, A. M., Bernstein, L., Smith, D. D., and Lai, L. L. (2013). Changing Patterns of Anal Canal Carcinoma in the United States. J. Clin. Oncol. JCO.2012.45.2524.

Nobbenhuis, M. A., Helmerhorst, T. J., van den Brule, A. J., Rozendaal, L., Voorhorst, F. J., Bezemer, P. D., Verheijen, R. H., and Meijer, C. J. (2001). Cytological regression and clearance of high-risk human papillomavirus in women with an abnormal cervical smear. Lancet Lond. Engl. 358, 1782-1783.

Piketty, C., Cochand-Priollet, B., Lanoy, E., Si-Mohamed, A., Trabelsi, S., Tubiana, R., Girard, P.-M., Weiss, L., Costagliola, D., and Valparaiso Study Group (2013). Lack of regression of anal squamous intraepithelial lesions despite immune restoration under cART. AIDS Lond. Engl. 27, 401-406.

Schiffman, M., Castle, P. E., Jeronimo, J., Rodriguez, A. C., and Wacholder, S. (2007). Human papillomavirus and cervical cancer. Lancet Lond. Engl. 370, 890-907.

Sozen, H., Namazov, A., Cakir, S., Akdemir, Y., Vatansever, D., and Karateke, A. (2014). Pregnancy outcomes after cold knife conization related to excised cone dimensions. A retrospective cohort study. J. Reprod. Med. 59, 81-86.

Sterling, J. c., Handfield-Jones, S., and Hudson, P. m. (2001). Guidelines for the management of cutaneous warts. Br. J. Dermatol. 144, 4-11.

Stratton, K. L., and Culkin, D. J. (2016). A Contemporary Review of HPV and Penile Cancer. Oncol. Williston Park N 30, 245-249.

Sunesen, K. G., Nørgaard, M., Thorlacius-Ussing, O., and Laurberg, S. (2010). Immunosuppressive disorders and risk of anal squamous cell carcinoma: a nationwide cohort study in Denmark, 1978-2005. Int. J. Cancer 127, 675-684.

Syrjänen, S. (2010). The role of human papillomavirus infection in head and neck cancers. Ann. Oncol. Off. J. Eur. Soc. Med. Oncol. ESMO 21 *Suppl* 7, vii243-245.

Syrjänen, K., Väyrynen, M., Castrén, O., Mäntyjärvi, R., Pyrhönen, S., and Yliskoski, M. (1983). Morphological and immunohistochemical evidence of human papilloma virus (HPV) involvement in the dysplastic lesions of the uterine cervix. Int. J. Gynaecol. Obstet. Off. Organ Int. Fed. Gynaecol. Obstet. 21, 261-269.

Wang, L., Yi, T., Kortylewski, M., Pardoll, D. M., Zeng, D., and Yu, H. (2009). IL-17 can promote tumor growth through an IL-6-Stat3 signaling pathway. J. Exp. Med. 206, 1457-1464.

Weis, S. E. (2013). Current treatment options for management of anal intraepithelial neoplasia. OncoTargets Ther. 6, 651-665.

The invention claimed is:

1. A method of treating a chronic infection caused by one or more human papillomaviruses (HPVs), selected from warts, condylomata, laryngeal papillomatosis and epidermodysplasia verruciformis, the method, comprising administering an effective amount of an antibody that specifically binds interleukin-17A (IL-17A) to a subject in need thereof, said antibody being an inhibitor or an antagonist of IL-17 signalling pathway,
said antibody being selected from the group consisting in Secukinumab and Ixekizumab.

2. The method according to claim 1, wherein said antibody is administered locally or systemically.

3. The method according to claim 1, wherein said antibody is Secukinumab administered subcutaneously with a 300 mg dose once a week for five weeks, then every four weeks.

* * * * *